United States Patent [19]

Paslean et al.

[11] Patent Number: 4,487,987

[45] Date of Patent: Dec. 11, 1984

[54] METHOD OF DECOLORIZING MIXTURES OF AMINOETHYLPIPERAZINE, A POLYOXYPROPYLENEDIAMINE AND ALKYLPHENOLS WITH N,N-DIETHYLHYDROXYLAMINE

[75] Inventors: James H. Paslean, Port Neches; Charles S. Steele, Nederland, both of Tex.

[73] Assignee: Texaco Inc., White Plains, N.Y.

[21] Appl. No.: 502,881

[22] Filed: Jun. 9, 1983

[51] Int. Cl.³ ............................................. C07C 37/68
[52] U.S. Cl. ..................................... 568/756; 568/749; 568/750; 544/402
[58] Field of Search ..................... 568/749, 750, 756; 544/402

[56] References Cited

U.S. PATENT DOCUMENTS 4,356,330 10/1982 Cuscurida et al. ................. 568/756
4,386,224 5/1983 Deetman ............................ 568/703

FOREIGN PATENT DOCUMENTS 0165332 10/1982 Japan ................................. 568/757

*Primary Examiner*—Werren B. Lone
*Attorney, Agent, or Firm*—Jack H. Park; Kenneth R. Priem; David L. Mossman

[57] ABSTRACT

A method of eliminating color-causing impurities in mixtures of aminoethylpiperazine, polyoxypropylenediamines and alkylphenols by treatment with N,N-diethylhydroxylamine is described. These alkylphenols such as nonylphenol are used in epoxy resins in the automotive and electronics industry. Discoloration of the phenol and subsequent resin occurs if the phenol is not treated with N,N-diethylhydroxylamine. Quantities on the order of 20 to 500 ppm are effective. The decolorization reaction may be conducted at a temperature in the range from about 25° to 50° C.

4 Claims, No Drawings

METHOD OF DECOLORIZING MIXTURES OF AMINOETHYLPIPERAZINE, A POLYOXYPROPYLENEDIAMINE AND ALKYLPHENOLS WITH N,N-DIETHYLHYDROXYLAMINE

BACKGROUND OF THE INVENTION

1. Field of the Invention

The invention relates to methods for treating mixtures of alkyl substituted phenols so that they will not cause discoloration when used in epoxy resins and more particularly relates to methods of treating mixtures of alkyl substituted phenols by means of the addition of N,N-diethylhydroxylamine.

2. Description of Other Related Methods in the Field

Many decolorizing agents now in use remove color by physical adsorption. The most common materials to remove color by this means are represented by charcoals, blacks (such as carbon black), clays and earths. Other compounds remove color by chemical reaction and are frequently more specific as to the materials they can remove color from than the physical adsorption agents. While attempts have been made to predict compound colors, such as by electronegative or steric contributions of substituents to aromatic rings, numerous exceptions to rules relating color to structure require color prediction to be based largely on empirical observations, see Griffiths, John; *Colour and Constitution of Organic Molecules;* London: Academic Press (1976), pp. 89–90. As a result, attempts to remove color from a specific compound tend to be strictly trial and error operations.

Specific examples may be seen in the decolorization of amines. U.S. Pat. No. 3,723,529 describes the decolorization of polyethylene polyamines through the use of a heated activated carbon treatment. The decoloration of ethylene amines may also be accomplished by heating the ethylene amines with zinc, aluminum or tin, or a combination thereof together with sodium hydroxide and/or potassium hydroxide according to the method described in Japanese Kokai 69-2209.

Activated carbon is frequently used as a method for purifying drinking water. Water may also be decolorized and decontaminated by contact with ozone as noted by R. D. Gabovich, et al. in *Gig. Sanit.* Vol. 34, No. 6, 1969, pp. 18–22 (Chemical Abstracts citation 71:53407k).

Other materials are well known as decolorizers; for example, ion-exchange resins. J. C. Abram, et al., in *Sucr. Belge/Sugar Ind. Abstr.* Vol. 90, No. 11, 1971, pp. 525–32 (CA 76:128256), describe color removal in substances such as polyethylene glycol and phenol by means of ion-exchange resins. U.S. Pat. No. 3,660,317 discloses that ion-exchange resin beads may be used to decolorize and deodorize materials and absorb ammonia. Ion-exchange resins may also be used to remove the metallic impurities from bis(2-hydroxyethyl) terephthalate by the method described in French Pat. No. 1,566,485 (CA 72:3241). Tertiary-aminocyclobutanes that have electronegative substituents have been found to be useful color stabilizers and antioxidants in gasoline according to U.S. Pat. No. 3,369,024.

A number of methods have been devised for purifying phenols and substituted phenols. For example, U.S. Pat. No. 3,437,699 reveals that phenol may be purified of color-forming impurities by treatment with hydrogen in the presence of a hydrogenation catalyst such as nickel-molybdenum. Mixtures containing o-hydroxybenzoic acids and saturated aliphatic polybasic acids and/or polybasic phosphoric acids or phosphoric acid esters may be added to phenol to give a color-stable product according to French Pat. No. 1,502,518 (CA 70:11340).

Mono- and dicarboxylic acids are effective to prevent the discoloration of phenols such as 2,6-diisopropylphenol according to Netherlands Appl. No. 6,516,378 (CA 67:2878). Compounds somewhat similar to those decolorized by the instant invention are p-tert-butylphenol and nonylphenol which may be decolorized by the addition of small amounts of hydrazine or hydrazine hydrate as described in Japanese Kokai 77–68,134 (CA 87:151841). Urban, et al. in *Sb. Pr. Vyzk. Chem. Vyuziti Uhli, Dehtu Ropy,* No. 10, 1970, pp. 65–78 (CA 74:22497), note that hydrazine hydrate improved the color stability of mixed monohydric phenols only in the absence of iron. The addition of powdered iron or an iron strip to alkylphenols such as 2,4-di-t-butylphenol and triisopropylphenol prevents coloration as French Pat. No. 1,597,867 discloses (CA 74:76170). Brominating phenols such as 4,4'-isopropylidenediphenol makes products of improved color and purity through the method of U.S. Pat. No. 3,546,302. Further, U.S. Pat. No. 3,454,654 discloses that 2,6-di-t-butyl-4-cresol may be used as a color stabilizer in the dibromination of phenol.

Color removal from substituted phenol polymers, such as poly(2,6-dimethyl-1,4-phenylene ether) may be effected by treating them with a reducing agent such as lithium aluminum hydride, sodium borohydride or sodium hydride as noted in Japanese Kokai No. 71-06,869 (CA 76:114121). Addition of ammonium acetate and other such compounds can decolorize phenol-aromatic hydrocarbon-aldehyde resins as described in Japanese Kokai No. 71-02,897 (CA 76:34873). Further, Japanese Kokai No. 74-31,631 (CA 81:25366) discloses a method of producing p-alkylphenols without color by means of a distillation process. The decolorization of dialkylolalkylphenols, such as 2,6-dimethylol-4-nonylphenol, may be accomplished by adding dilute solutions of oxalic acid as shown in U.S. Pat. No. 3,306,938. Alkylphenol-ethylene oxide adducts and the sulfates thereof may be purified and decolorized by contacting the materials with an alkali metal borohydride as described in U.S. Pat. Nos. 3,375,284 and 3,687,999.

U.S. Pat. No. 4,337,369 teaches a method for eliminating color-causing impurities in mixtures of t-butyl alkylphenols by treatment with trioxane at about 100° C. Finally, another method of decolorizing mixtures of t-butyl alkylphenols, this time by treatment with N-(2-hydroxyethyl)oxazolidine at about 90° C. is described in U.S. Pat. No. 4,356,330 (see also, the references cited in these last two patents).

SUMMARY OF THE INVENTION

The invention is a method for decolorizing mixtures of aminoethylpiperazine, polyoxypropylenediamine and alkylphenols comprising adding a portion of N,N-diethylhydroxylamine to the alkylphenol.

DETAILED DESCRIPTION OF THE PREFERRED EMBODIMENTS OF THE INVENTION

The alkylphenol may be produced by using an anionic ion-exchange resin catalyst such as a sulfonic acid resin to react an alkylene monomer or polymer with phenol. Alternatively, the alkylphenol may be made using boron trifluoride as a catalyst. Alkylphenols may also be made according to the methods disclosed in U.S. Pat. Nos. 4,138,591 and 4,202,199, incorporated by reference herein. It is anticipated that this method would be effective for alkylphenols produced by any method. However, the alkyl substituent on the phenol should have from 4 to 20 carbon atoms. Especially preferred is nonylphenol.

Alkylphenols are useful in the production of epoxy resins for use in the automotive and plastics industry. As a result, the resins and alkylphenols should have very little color to be aesthetically pleasing and meet specifications.

The compound found useful as a decolorizing agent herein is N,N-diethylhydroxylamine (DEHA). A number of other compounds structurally similar to DEHA were tested to try to decolorize alkylphenols, although none of them worked. The other similar compounds tested were monoethanolamine, diethanolamine, triethanolamine, 2-(2-aminoethoxy)ethanol (also known as DIGLYCOLAMINE ® agent sold by Texaco Chemical Company), morpholine, N-aminoethylpiperazine and N-nitrosophenylhydroxylamine. It is surprising that DEHA has been found to be effective at decolorizing alkylphenols when these similar compounds are ineffective.

The effective concentration range of DEHA is from about 20 to 500 ppm by weight based on the quantity of alkylphenol (0.002 to 0.05 wt. %). This range could be extended to 1,000 ppm (0.1 wt. %) but no additional benefit would be expected. DEHA is a commercially available chemical commonly used as a photographic developer, an antioxidant and a corrosion inhibitor.

If a formal decolorization step is performed, it is preferred that the temperature for the decolorization reaction be in the range from ambient temperature to about 120° F. (from about 25° to 50° C.). The nonylphenol treated with very low concentrations of DEHA has a limited "shelf life" at 120° F. and higher. As will be shown, other common additives such as aminoethylpiperazine (AEP, an epoxy resin curing agent) and JEFFAMINE ® D-230 amine (a polyoxypropylenediamine having a molecular weight of about 230 made by Texaco Chemical Company used as an epoxy resin curing agent) can be incorporated into the treated alkylphenol without any detrimental color effect.

The invention in its simplest terms involves simply adding DEHA to the alkylphenol or a mixture containing alkylphenols, without a formal "reaction step" at an elevated temperature. The same decolorizing benefit may be achieved by simply adding the DEHA to the epoxy resin mixture. Alternatively, DEHA may be added to the AEP or to JEFFAMINE D-230 amine before the resin reaction to give the same end result of color improvement in the resin. DEHA may also be added as just an additional ingredient with the same good results.

The amine color test used in the examples involves the visual inspection of the color of a mixture of alkylphenol, AEP and JEFFAMINE D-230 in a weight ratio of 68:12:20. The actual color is determined by measuring the blended color on the Pt-Co color scale and then making a subjective interpretation of the hue. A passing score would be less than 60 Pt-Co color with a light to medium green hue. Failures would include blends having pink, brown, orange or bronze hues. The samples treated with DEHA in the examples have passed with less than 60 Pt-Co color and acceptable hues, but those samples that failed had unacceptable hues.

The method of this invention will be further illustrated by the following examples which are not intended to limit its spirit or scope.

EXAMPLE I

Nonylphenol was mixed with 130 ppm of N,N-diethylhydroxylamine and stored at 120° F. for twelve days. The treated product was mixed with aminoethylpiperazine and JEFFAMINE D-230 in a ratio of 68:12:20 parts by weight. The mixture passed our special amine color test. Untreated nonylphenol failed the amine color test.

EXAMPLE II

Nonylphenol was mixed with 24, 62 and 130 ppm N,N-diethylhydroxylamine and stored at 120° F. After eighteen days, 68 grams of a blend were mixed with 12 grams of aminoethylpiperazine and 20 grams of JEFFAMINE D-230. Each mixture passed the amine color test while the control nonylphenol product failed the amine color test.

The compounds monoethanolamine, diethanolamine, triethanolamine, morpholine, 2-(2-aminoethoxy)ethanol, aminoethylpiperazine and N-nitrosophenylhydroxylamine were similarly tested for color-removing ability and found to be ineffective.

EXAMPLE III

DEHA can be added as a component in the blend. For example, 136 grams of nonylphenol was mixed with 24 grams of AEP, 40 grams of JEFFAMINE D-230 amine and 0.02 grams of DEHA. The blend passed the amine color test.

EXAMPLE IV

DEHA can also be added as a component of AEP or JEFFAMINE D-230 amine.

For example, a mixture of 197 ppm DEHA in AEP was prepared. Twelve grams of this mixture was added to 20 grams of JEFFAMINE D-230 and 68 grams of nonylphenol. This blend passed the amine color test with a 40 Pt-Co color and a light green hue.

EXAMPLE V

A mixture of 223 ppm DEHA in JEFFAMINE D-230 amine was prepared. Twenty grams of this mixture was added to 12 grams of AEP and 68 grams of nonylphenol. This blend passed the amine color test with a 35 Pt-Co color and a light green hue.

Many modifications may be made in the method of this invention without departing from the spirit and scope thereof which are defined only in the appended claims. For example, the modes of addition, temperatures and alkylphenols could be changed to optimize the process.

We claim:

1. A method for decolorizing mixtures of aminoethylpiperazine, a polyoxypropylenediamine and alkylphenols comprising
adding from 20 to 500 ppm by weight of N,N-diethylhydroxylamine to the mixture of aminoethylpiperazine, polyoxypropylenediamine and alkylphenol, where the alkylphenol has from 4 to 20 carbon atoms in the alkyl substituent.

2. The method of claim 1 in which the alkylphenol is nonylphenol.

3. A method for decolorizing mixtures of aminoethylpiperazine, a polyoxypropylenediamine and alkylphenols comprising reacting a mixture of aminoethylpiperazine, a polyoxypropylenediamine and an alkylphenol, where the alkyl substituent on the alkylphenol has from 4 to 20 carbon atoms, with from 20 to 500 ppm by weight of N,N-diethylhydroxylamine at a temperature in the range of about 25° to 50° C. in a homogeneous liquid phase reaction.

4. The method of claim 3 where the alkylphenol is nonylphenol and contains a weight ratio of nonylphenol: aminoethylpiperazine: a polyoxypropylenediamine of about 230 molecular weight of about 68:12:20.

* * * * *